US 9,921,140 B2

(12) United States Patent
Calio et al.

(10) Patent No.: US 9,921,140 B2
(45) Date of Patent: *Mar. 20, 2018

(54) AIR SAMPLE TRACKING SYSTEM AND METHOD

(71) Applicant: Veltek Associates, Inc., Malvern, PA (US)

(72) Inventors: Rosario S. Calio, Exton, PA (US); Mark A. Phillips, King of Prussia, PA (US); John Joyce, Frazer, PA (US)

(73) Assignee: Veltek Associates, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/599,229

(22) Filed: May 18, 2017

(65) Prior Publication Data

US 2017/0254730 A1    Sep. 7, 2017

Related U.S. Application Data

(63) Continuation of application No. 15/249,044, filed on Aug. 26, 2016, now Pat. No. 9,658,140, which is a
(Continued)

(51) Int. Cl.
*G01T 1/20* (2006.01)
*G01N 1/22* (2006.01)
(Continued)

(52) U.S. Cl.
CPC ......... *G01N 1/2273* (2013.01); *G01N 1/2208* (2013.01); *G01N 1/24* (2013.01);
(Continued)

(58) Field of Classification Search
CPC .............. G01T 1/20; G01T 1/248; G01T 7/00
(Continued)

(56) References Cited

U.S. PATENT DOCUMENTS

| 793,668 A | 7/1905 | Lepley |
| 4,091,674 A | 5/1978 | Amey |

(Continued)

FOREIGN PATENT DOCUMENTS

| CN | 1598591 A | 3/2005 |
| CN | 102066897 A | 5/2011 |

(Continued)

OTHER PUBLICATIONS

Veltek Associates, Inc., One Touch Command™ SMA™ Microbial Air Sampling Systems Brochure, Revised Dec. 2002, 4 pgs., Malvern, Pennsylvania.
(Continued)

*Primary Examiner* — David Porta
*Assistant Examiner* — Meenakshi Sahu
(74) *Attorney, Agent, or Firm* — Blank Rome LLP

(57) ABSTRACT

A system for tracking one or more subjects for collecting airborne contaminants. The system includes one or more subjects configured to collect air contaminants. Each of the one or more subjects includes an identification tag encoded with identification information identifying the each subject. The system further includes an identification reader configured to decode the identification information encoded within the identification tag of a scanned one of the one or more identification tags. A computer receives and stores the decoded identification information in a record in a database. The computer may also receive and stored an identification code for a user who scanned the scanned identification tag in the record in the database. Additional records in the database are created each time the identification tag of one of the one or more subjects is scanned. The one or more subjects are thereby tracked as they collect airborne contaminants and are incubated.

20 Claims, 8 Drawing Sheets

Related U.S. Application Data continuation of application No. 14/728,783, filed on Jun. 2, 2015, now Pat. No. 9,448,144, which is a continuation of application No. 14/196,392, filed on Mar. 4, 2014, now Pat. No. 9,046,453, which is a continuation of application No. 13/446,572, filed on Apr. 13, 2012, now Pat. No. 8,701,980.

(60) Provisional application No. 61/552,264, filed on Oct. 27, 2011.

(51) Int. Cl.
| | | |
|---|---|---|
| *G06K 19/077* | (2006.01) | |
| *G01N 1/24* | (2006.01) | |
| *G06K 7/14* | (2006.01) | |
| *G06F 17/30* | (2006.01) | |
| *G01N 1/26* | (2006.01) | |
| *G06K 19/06* | (2006.01) | |
| *G01N 1/02* | (2006.01) | |

(52) U.S. Cl.
CPC ......... *G01N 1/26* (2013.01); *G06F 17/30353* (2013.01); *G06F 17/30368* (2013.01); *G06K 7/1413* (2013.01); *G06K 19/06028* (2013.01); *G06K 19/07758* (2013.01); *G01N 2001/021* (2013.01)

(58) Field of Classification Search
USPC ........................................................ 250/366
See application file for complete search history.

(56) References Cited

U.S. PATENT DOCUMENTS

| | | | |
|---|---|---|---|
| 4,604,111 A | 8/1986 | Natale | |
| 4,663,293 A | 5/1987 | Hempel et al. | |
| 4,813,984 A | 3/1989 | Griffis | |
| 5,421,214 A | 6/1995 | Burgdorfer | |
| 5,553,496 A | 9/1996 | Nishiyama et al. | |
| 5,591,974 A | 1/1997 | Troyer et al. | |
| 5,635,403 A | 6/1997 | Bailey | |
| 5,645,480 A | 7/1997 | Spengler | |
| 5,831,182 A | 11/1998 | Swenson | |
| 5,838,008 A | 11/1998 | Esler et al. | |
| 6,025,200 A | 2/2000 | Kaish et al. | |
| 6,125,710 A | 10/2000 | Sharp | |
| 6,167,107 A | 12/2000 | Bates | |
| 6,167,766 B1 | 1/2001 | Dunn et al. | |
| 6,216,548 B1 | 4/2001 | Park et al. | |
| 6,230,080 B1 | 5/2001 | Lee et al. | |
| 6,295,864 B1 | 10/2001 | You et al. | |
| 6,425,297 B1 | 7/2002 | Sharp | |
| 6,425,298 B1 | 7/2002 | Jackson et al. | |
| 6,514,721 B2 | 2/2003 | Spurrell | |
| 6,532,835 B1 | 3/2003 | Saaski et al. | |
| 6,692,953 B1 | 2/2004 | Sugita et al. | |
| 6,867,682 B2 | 3/2005 | Reinhardt et al. | |
| 7,667,839 B2 | 2/2010 | Bates | |
| 7,940,188 B2 | 5/2011 | Calio et al. | |
| 7,973,668 B2 | 7/2011 | Calio et al. | |
| 8,006,542 B2 | 8/2011 | Jones, Jr. | |
| 8,169,330 B2 | 5/2012 | Calio et al. | |
| 8,188,874 B2 | 5/2012 | Calio | |
| 8,701,980 B2 | 4/2014 | Calio et al. | |
| 9,658,140 B2 * | 5/2017 | Calio ................... | G01N 1/2273 |
| 2001/0030642 A1 | 10/2001 | Sullivan et al. | |
| 2002/0070862 A1 | 6/2002 | Francis et al. | |
| 2004/0044493 A1 | 3/2004 | Coulthard | |
| 2006/0000296 A1 | 1/2006 | Salter | |
| 2008/0148816 A1 | 6/2008 | Groves | |
| 2008/0158543 A1 | 7/2008 | Puskas et al. | |
| 2009/0149340 A1 | 6/2009 | True | |
| 2010/0283620 A1 | 11/2010 | Calio et al. | |
| 2010/0297602 A1 | 11/2010 | Jones, Jr. | |
| 2011/0192213 A1 * | 8/2011 | Zimmerman ............ | A01K 5/02 73/23.3 |
| 2012/0186774 A1 * | 7/2012 | Matsuoka .......... | G05D 23/1904 165/11.1 |
| 2014/0051118 A1 | 2/2014 | Matthiesen et al. | |
| 2014/0060155 A1 | 3/2014 | Hering et al. | |

FOREIGN PATENT DOCUMENTS

| | | |
|---|---|---|
| EP | 2343528 A2 | 7/2011 |
| WO | WO-03/060062 A2 | 7/2003 |
| WO | WO-2009100184 A1 | 8/2009 |
| WO | WO-2010105161 A1 | 9/2010 |
| WO | WO-2011103145 A1 | 8/2011 |

OTHER PUBLICATIONS

International Application No. PCT/US2009/033163, International Search Report and Written Opinion, dated Jun. 24, 2009, 7 pp.
International Application No. PCT/US2010/027145, International Search Report and Written Opinion, dated May 12, 2010, 10 pp.
International Application No. PCT/US2011/025021, International Search Report and Written Opinion, dated Mar. 17, 2011, 5 pp.

* cited by examiner

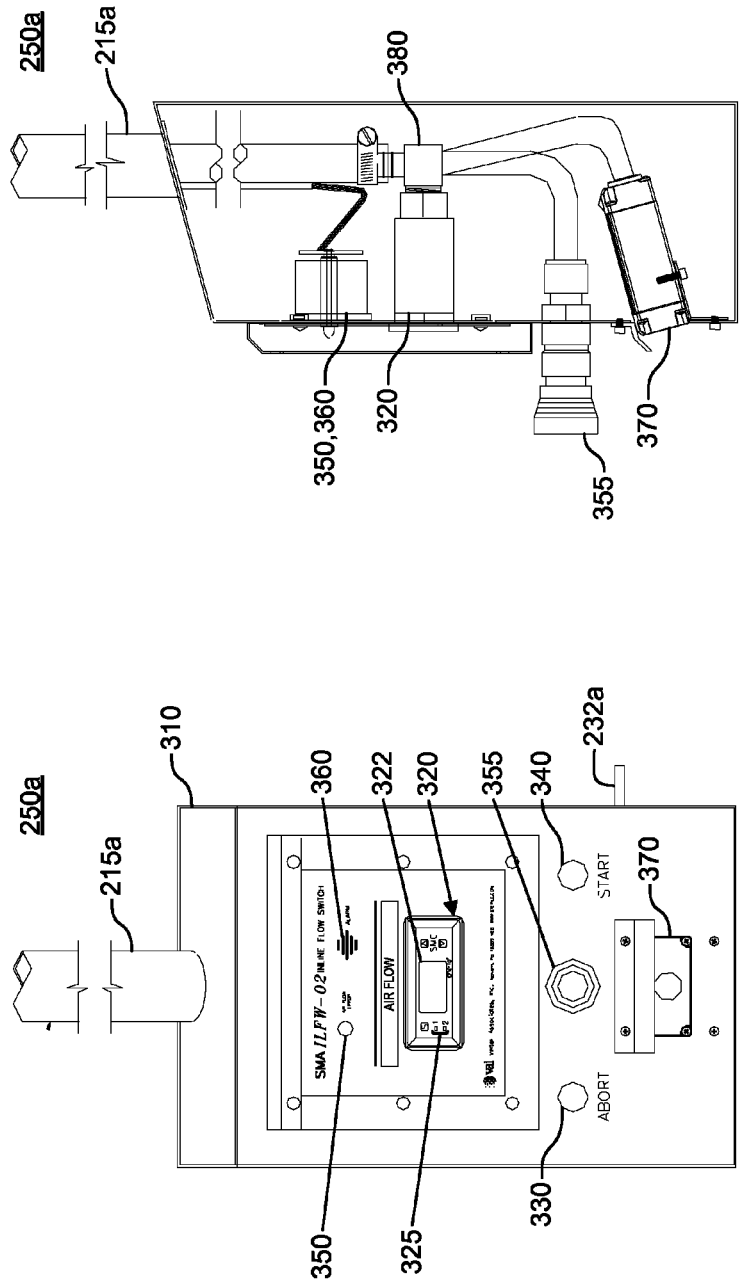

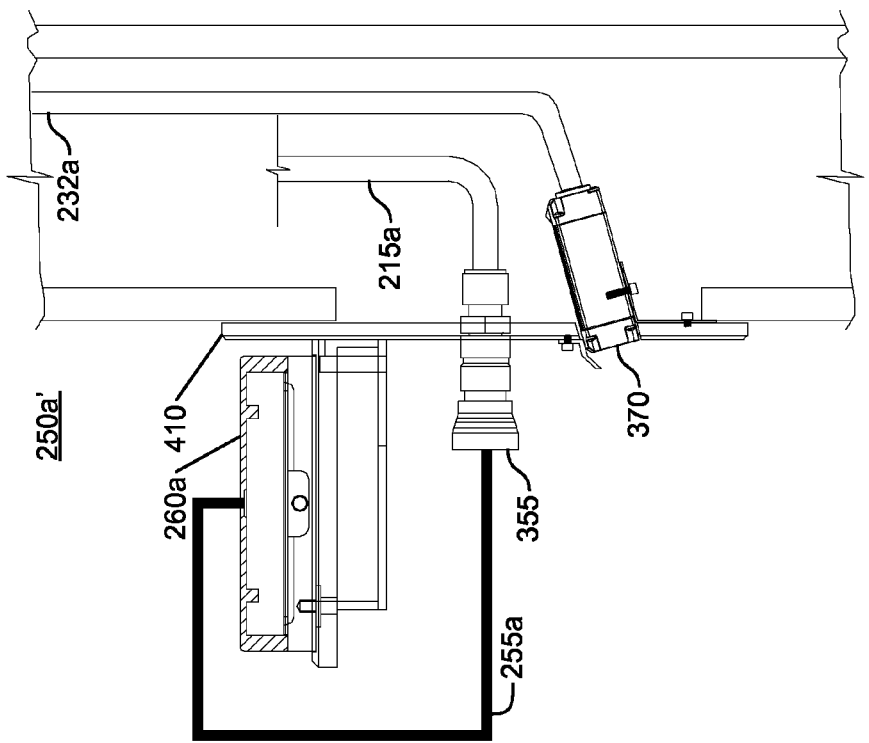
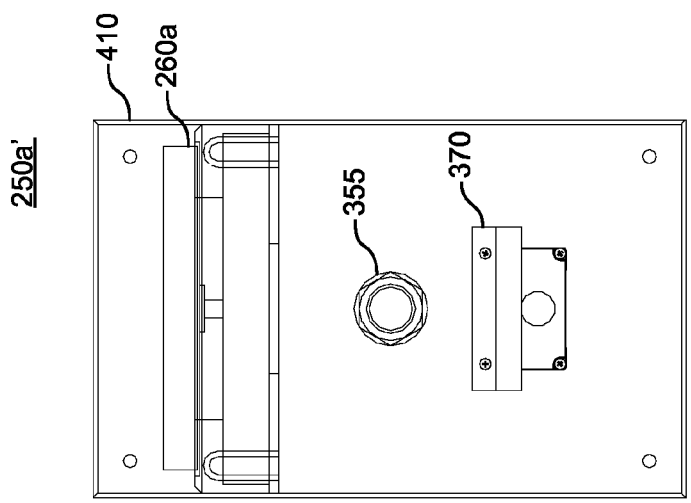
FIG. 4B
FIG. 4A

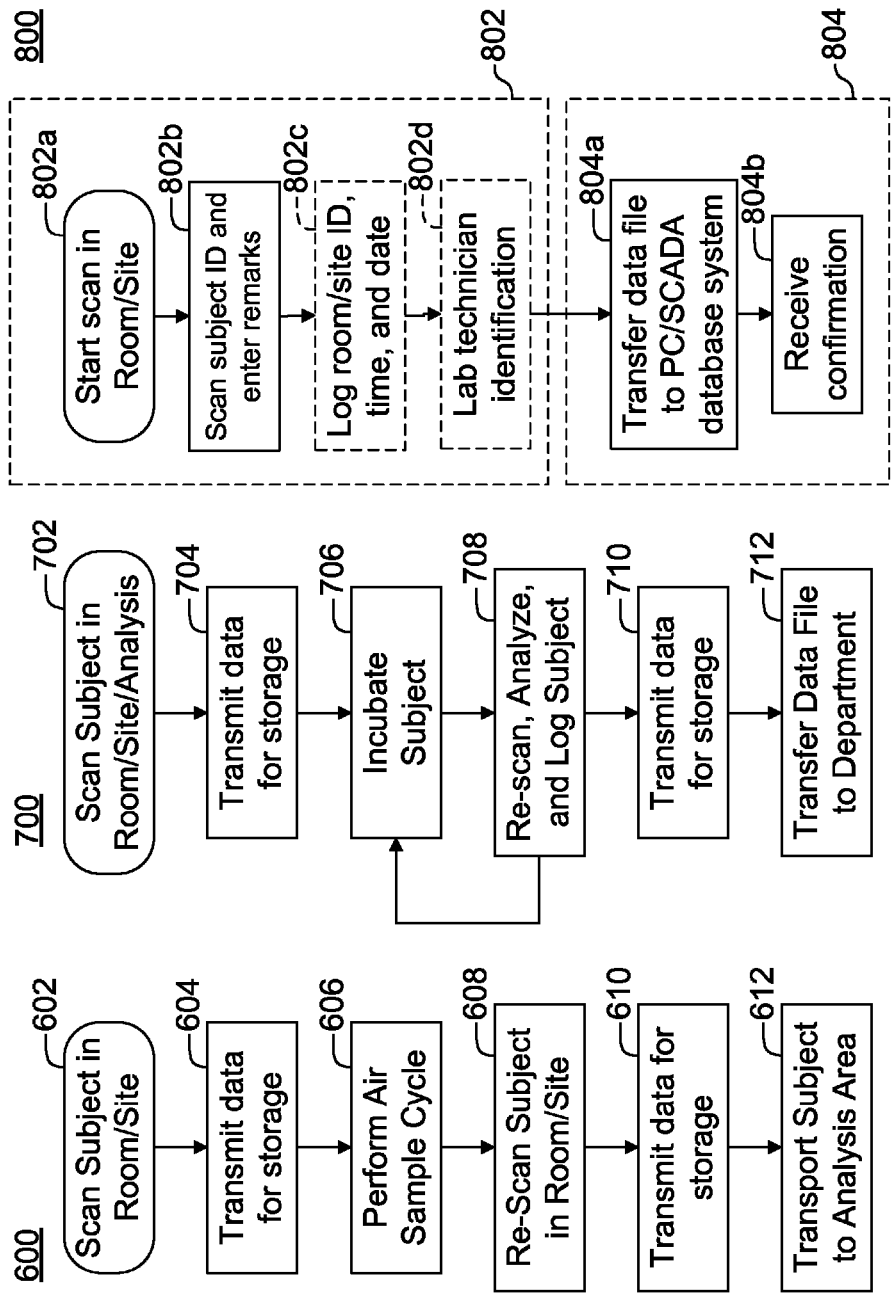

| | SCANNED 910 | | LOCATION 920 | | PLATE AND TECH ID 930 | | REMARKS 940 |
|---|---|---|---|---|---|---|---|
| | 910a<br>Date | 910b<br>Time | 920a<br>Room | 920b<br>Site | 930a<br>Plate ID | 930b<br>Tech ID | 940a<br>Ex: 1 CFM error, abort sample, etc. |
| 1 | 2/16/2011 | 10:22 PM | 119 | Bench | SMA 001 | Tom | |
| 2 | 2/16/2011 | 11:25 PM | 119 | Bench | SMA 001 | John | |
| 3 | 2/16/2011 | 11:30 PM | 104 | Incubation | SMA 001 | Sarah | |
| 4 | 2/17/2011 | 1:30 AM | 104 | Incubation | SMA 001 | Sarah | 2 colonies - send alert |
| 5 | 2/21/2011 | 1:35 AM | 104 | Incubation | SMA 001 | Ralph | 3 colonies - send alarm |
| 6 | 2/16/2011 | 10:26 PM | 119 | LFM | SMA 005 | Tom | |
| 7 | 2/16/2011 | 11:30 PM | 119 | LFM | SMA 005 | Tom | |
| 8 | 2/16/2011 | 11:45 PM | 104 | Incubation | SMA 005 | Harry | 2 colonies - ok |
| 9 | 2/17/2011 | 5:00 AM | 104 | Incubation | SMA 005 | Harry | 5 colonies - send alert |
| 10 | 2/18/2011 | 7:00 PM | 104 | Incubation | SMA 005 | Jane | |
| 11 | 2/16/2011 | 1:00 PM | 2120 | Fill 1 | SMA 010 | Mike | |
| 12 | 2/16/2011 | 2:15 PM | 2120 | Fill 1 | SMA 010 | Mike | |
| 13 | 2/16/2011 | 2:30 PM | 104 | Incubation | SMA 010 | Sarah | No colonies |
| 14 | 2/17/2011 | 2:30 PM | 104 | Incubation | SMA 010 | Sarah | 1 colony - send alert |
| 15 | 2/18/2011 | 1:35 PM | 104 | Incubation | SMA 010 | Jane | |
| 16 | 2/16/2011 | 1:10 PM | 2120 | Fill 2 | SMA 011 | Mike | |
| 17 | 2/16/2011 | 1:15 PM | 2120 | Fill 2 | SMA 011 | Mike | |
| 18 | 2/16/2011 | 1:20 PM | 104 | Incubation | SMA 011 | Sarah | |
| 19 | 2/17/2011 | 1:30 PM | 104 | Incubation | SMA 011 | Sarah | 1 colony - ok |
| 20 | 2/18/2011 | 1:29 PM | 104 | Incubation | SMA 011 | Jane | 1 colony - ok |

AIR SAMPLE TRACKING SYSTEM AND METHOD

CROSS REFERENCE TO RELATED APPLICATIONS

This application is a continuation of U.S. Pat. No. 9,658, 140 filed Aug. 26, 2016, which is a continuation of U.S. Pat. No. 9,448,144 filed Jun. 2, 2015 which is a continuation of U.S. Pat. No. 9,046,453, filed Mar. 4, 2014, which is a continuation of U.S. Pat. No. 8,701,980, filed Apr. 13, 2012, which claims the benefit of U.S. Provisional Application No. 61/552,264, entitled "Air Sample Tracking System and Method" and filed on Oct. 27, 2011, the entire disclosures of which are hereby incorporated by reference in their entirety.

FIELD OF INVENTION

The present invention relates to devices and methods for monitoring airborne contaminants. In particular, the present invention relates to devices and methods for logging data relating to contaminant-collection subjects, e.g., agar plates, as they collect airborne contaminants, are incubated, and are subject to air sampling.

BACKGROUND OF THE INVENTION

Clean rooms found in manufacturing, research, and other facilities are typically classified into two broad categories based on the static air pressure inside the rooms relative to atmospheric pressure and/or based on the air pressure in spaces adjacent the clean rooms. A positive air pressure room is maintained at an absolute air pressure greater than atmospheric pressure, greater than the air pressure in spaces adjacent the clean room, or both. The positive air pressure in such rooms is provided by pumping filtered and/or conditioned air into the rooms and controlling the flow of air out of the rooms. The adjacent spaces, which may be manufacturing facilities or offices, are typically maintained at or close to atmospheric pressure by heating, ventilation, and air conditioning (HVAC) systems, or by providing an opening to the environment that allows the adjacent spaces to equilibrate with atmospheric pressure. Thus, air flowing from the positive pressure clean room will flow toward the lower pressure in adjacent rooms or to the atmosphere.

When a positive air pressure clean room is breached, air flowing to adjacent spaces or the atmosphere is generally not a problem as long as airborne contaminants present in the clean room do not pose a potential adverse health effect to people in the adjacent spaces. Typically, the air inside clean rooms in which electronics, aerospace hardware, optical systems, military equipment, and defense-related research are manufactured or conducted may not contain airborne gases, vapors, and particulate matter at concentrations that present a safety or health concern to human health or the environment. However, that is not always the case, as other operations within those industries may generate contaminants that are above acceptable levels and, therefore, must be prevented from escaping the clean room without treatment.

A negative air pressure room is maintained at an absolute air pressure that is either less than atmospheric pressure, less than the air pressure in spaces adjacent the clean room, or both. The negative pressure is maintained by pumping air out of the room at a rate faster than that at which filtered and/or conditioned air is pumped into the room. Negative pressure rooms are often used when there is a concern that contaminants in the air in the room may pose a potential health threat to human health in adjacent spaces or the environment.

Notwithstanding the human health and environmental implications, certain types of manufacturing and research operations must be conducted within a positive air pressure clean room to satisfy regulatory requirements and industry-adopted good manufacturing and laboratory quality control standards. For example, state and federal regulations, including those promulgated by the National Institute for Occupational Safety and Health (NIOSH), may necessitate the use of positive or negative pressure clean rooms.

In particular, the U.S. Food & Drug Administration (FDA) requires that pharmaceutical production be done within the confines of clean rooms that provide for the validation and certification that manufactured batches of pharmaceutical products are being produced in a sanitary environment.

Positive and negative air pressure clean rooms have been used for many years. U.S. Pat. No. 4,604,111, for example, discloses a negative pressure apparatus and method for protecting the environment and populations from airborne asbestos and other particulate contamination inside a building, which includes an enclosure having a blower to pull air into a filtration unit inside the enclosure and dispel the filtered air to the atmosphere. U.S. Pat. No. 5,645,480 discloses the general features of a clean room.

Various FDA regulations and standards also specify requirements for air sampling and/or air monitoring equipment to be used inside clean rooms to verify or validate the cleanliness of the facility during certain drug manufacturing activities. The regulations also provide for electronic data recording, accuracy, precision, and record-keeping relating to monitoring the air quality within clean rooms. Similar requirements are imposed on other industries, such as the biotechnology industry.

U.S. Pat. No. 6,514,721 describes an air sampling device and method for collecting airborne pathogens and psychrometric data from a room or from remote air samples where the sample volume is electronically controlled by closely monitoring fan speed. That patent illustrates a device that draws room air into a sampling device using a pump, which causes pathogen-containing particulates in the air to impact a growth/inhibitor media (a solid, liquid, gel, or mixture thereof) stored in a dish that is positioned within the sampling device. The patent states that previous sampling devices could not achieve a constant volumetric air flow of better than +/−30% relative to a nominal or set-point flow rate, which caused a large variability in calculated concentrations of pathogens.

As U.S. Pat. No. 6,514,721 patent suggests, one of the keys to successfully monitoring the air quality within a clean room is to ensure that the air flow rate through the air sampling/monitoring devices is very accurately determined during the time when a volume of air is collected. That fact is also appreciated in U.S. Pat. No. 4,091,674, which discloses an electronically timed, positive displacement air sampling pump for use with a wide variety of air sample collecting devices and in a wide range of environmental conditions. The disclosed invention is said to provide accurate average flow rate, independently metered total volume, operating time register, and audible "rate fault" alarm. In that patent, accuracy is achieved by using a timing circuit coupled with a mechanical bellows.

U.S. Pat. No. 6,216,548 illustrates a control system flow chart for an air sampling device for use in a controlled environment. In particular, the patent discloses a controller logic that involves turning on a pump, checking pressure, monitoring sampling time, drawing air into the sampler, shutting off the pump, and checking for leaks in the lines. The patent also teaches using a purge system for purging the lines and associated air particulate sampler using a purge gas such as nitrogen gas. In that patent, air sampling only occurs at one location (e.g., a processing chamber for semiconductor devices).

SUMMARY OF THE INVENTION

In accordance with an aspect of the present invention there is provided a system for tracking one or more subjects. The system includes one or more subjects configured to collect air contaminants. Each of the one or more subjects includes an identification tag encoded with identification information identifying the each subject and other information regarding the each subject. The system further includes an identification reader configured to decode the identification information encoded within the identification tag of a scanned one of the one or more identification tags. A computer receives and stores the decoded identification information from the identification reader in a record in a database. The barcode scanner may be further configured to transmit location information identifying the location of the scanned one of the one or more identification tags. The location information is logged by the computer with the decoded identification information.

In accordance with another aspect of the present invention, there is provided a system for sampling air at a plurality of locations in a controlled environment. The system includes one or more air sampling devices, a vacuum source, a controller connected to the vacuum source, one or more subjects configured to collect air contaminants in the controlled environment, an identification reader, and a computer configured to receive data from the identification reader. The one or more air sampling devices are disposed in a controlled environment, the one or more air sampling devices each comprising a first identification reader. The controller is configured to be in separate air flow communication with the one or more air sampling devices via one or more respective vacuum air tubes. The controller includes a manifold configured to separately control an actual rate of air flow from the one or more air sampling devices to the vacuum source via each of the one or more respective vacuum air tubes to selectively direct air flow from each of the one or more respective vacuum air tubes to the vacuum source. The one or more subjects are configured to collect air contaminants in the controlled environment. Each of the one or more subjects includes an identification tag encoded with identification information identifying the each subject. The identification reader is configured to decode the identification information encoded within the identification tag of a scanned one of the one or more identification tags and to transmit such decoded information to the computer. The computer receives and stores the decoded identification information in a record in a database.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings:

FIG. 3A is front planar view of an inline flow control module which may be used in the system of FIG. 2, in accordance with an exemplary embodiment of the present invention;

FIG. 3B is a side cross-sectional view of the inline flow control module of FIG. 3A, in accordance with an exemplary embodiment of the present invention;

FIG. 4A is a front planar view of a wall panel disconnect which may be used in the system of FIG. 2, in accordance with an exemplary embodiment of the present invention;

FIG. 4B is a side cross-sectional view of the wall panel disconnect of FIG. 4A, in accordance with an exemplary embodiment of the present invention;

FIG. 6 illustrates an exemplary air sampling method, in accordance with an exemplary embodiment of the present invention;

FIG. 7 illustrates an exemplary incubation method, in accordance with an exemplary embodiment of the present invention;

FIG. 8 illustrates an exemplary method of tracking and logging information regarding one or more contaminant-collection subjects, in accordance with an exemplary embodiment of the present invention;

FIG. 9 illustrates an exemplary table stored in a database within the system of FIG. 2, the table logging information regarding one or more contaminant-collection subjects, in accordance with an exemplary embodiment of the present invention.

DETAILED DESCRIPTION OF THE INVENTION

Figure 1:
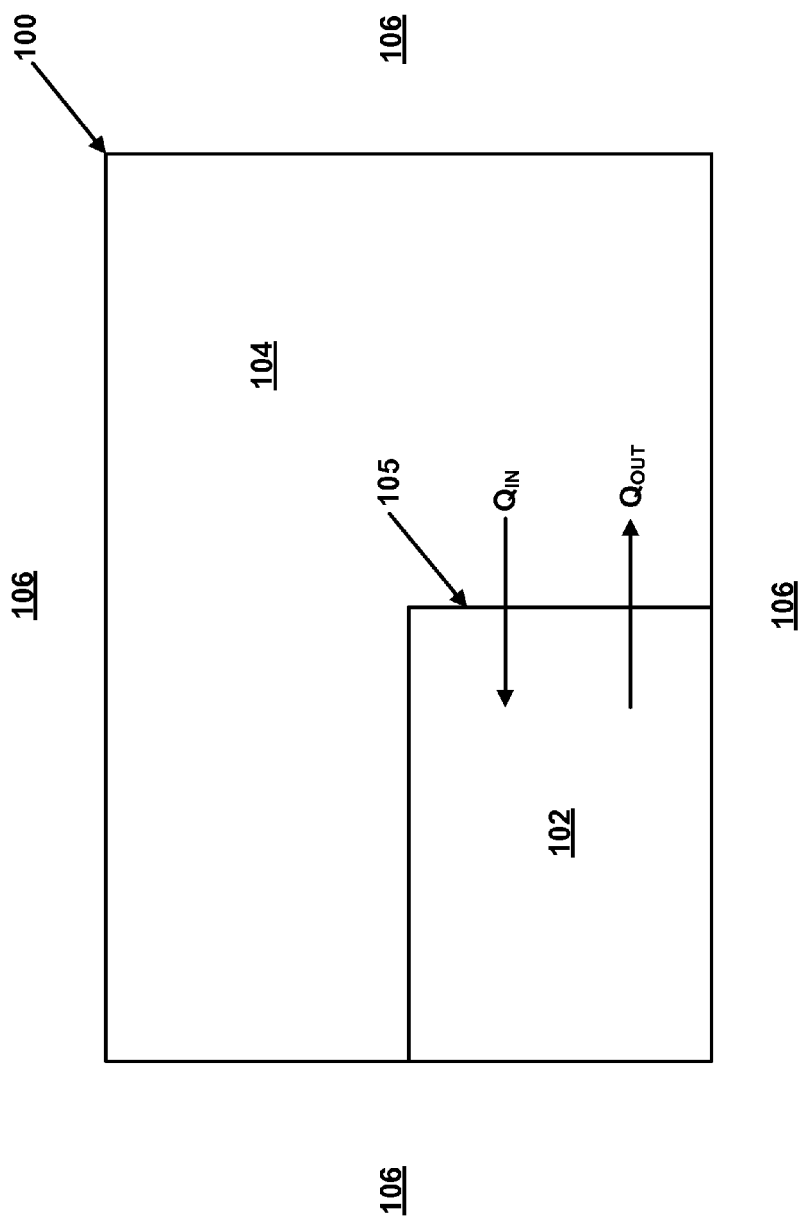
FIG. 1 is a schematic diagram of an exemplary facility having a clean room therein, in accordance with an exemplary embodiment of the present invention.

None of the conventional devices described above provide the degree of control, monitoring, reporting, modularity, and remote operation required in the modern clean room. For example, none of the conventional devices and air sampling methods described above utilizes multiple air sampling devices with inline flow switches at each air sampling device to separately and simultaneously measure the air flow realized at each individual air sampling device. Additionally, none of the conventional devices and air sampling methods described above provide the ability to simultaneously monitor and control a variable number of air sampling devices placed at different locations in a clean room from a single, central location that is remote from the air sampling devices. Finally, none of the conventional devices provide for electronic tracking and logging of data relating to subjects (e.g., agar plates) while they are collecting contaminants in the environment of a clean room or while they are under incubation or air sampling. Accordingly, there is also a need for an air sampling system and method that allows a user to separately and simultaneously track and log data regarding a plurality of contaminant-collection subjects while they are collecting contaminants in the environment of a clean room or while they incubated or subject to air sampling.

Several exemplary embodiments of the invention are described for illustrative purposes, it being understood that the invention may be embodied in other forms not specifically shown in the drawings.

Turning first to FIG. 1, shown therein is a schematic of an exemplary facility 100 having one or more clean rooms 102 therein, in accordance with an exemplary embodiment of the present invention. The clean room 102 is surrounded by an adjacent space 104 and the outdoor atmosphere 106. The adjacent space 104 may be one or more rooms within the same facility 100 in which the clean room 102 is located and that adjoin the clean room 102, such as, for example, a separate manufacturing room, another clean room, a finish and fill room, a research laboratory, offices, etc. The clean room 102 and adjacent space 104 are separated by a divider, such as a wall 105.

The clean room 102 in the exemplary facility 100 is capable of being maintained at an air pressure $P_1$ that is less than or greater than the air pressure $P_2$ of the adjacent space 104 and atmospheric air pressure $P_{ATM}$ of the outdoor atmosphere 106. That is accomplished by an HVAC system (not shown) that causes conditioned and filtered air to be pumped into the clean room 102 at a controlled flow rate $Q_{IN}$ as depicted in FIG. 1. Air inside the clean room 102 that is pumped out of or otherwise flows out of the clean room 102 is represented by $Q_{OUT}$. When the difference between $Q_{IN}$ and $Q_{OUT}$ (i.e., $Q_{IN}-Q_{OUT}$) is greater than zero, a positive pressure will be maintained in the clean room 102. And, when the difference between $Q_{IN}$ and $Q_{OUT}$ is less than zero, a negative pressure will be maintained in the clean room 102.

Figure 2:
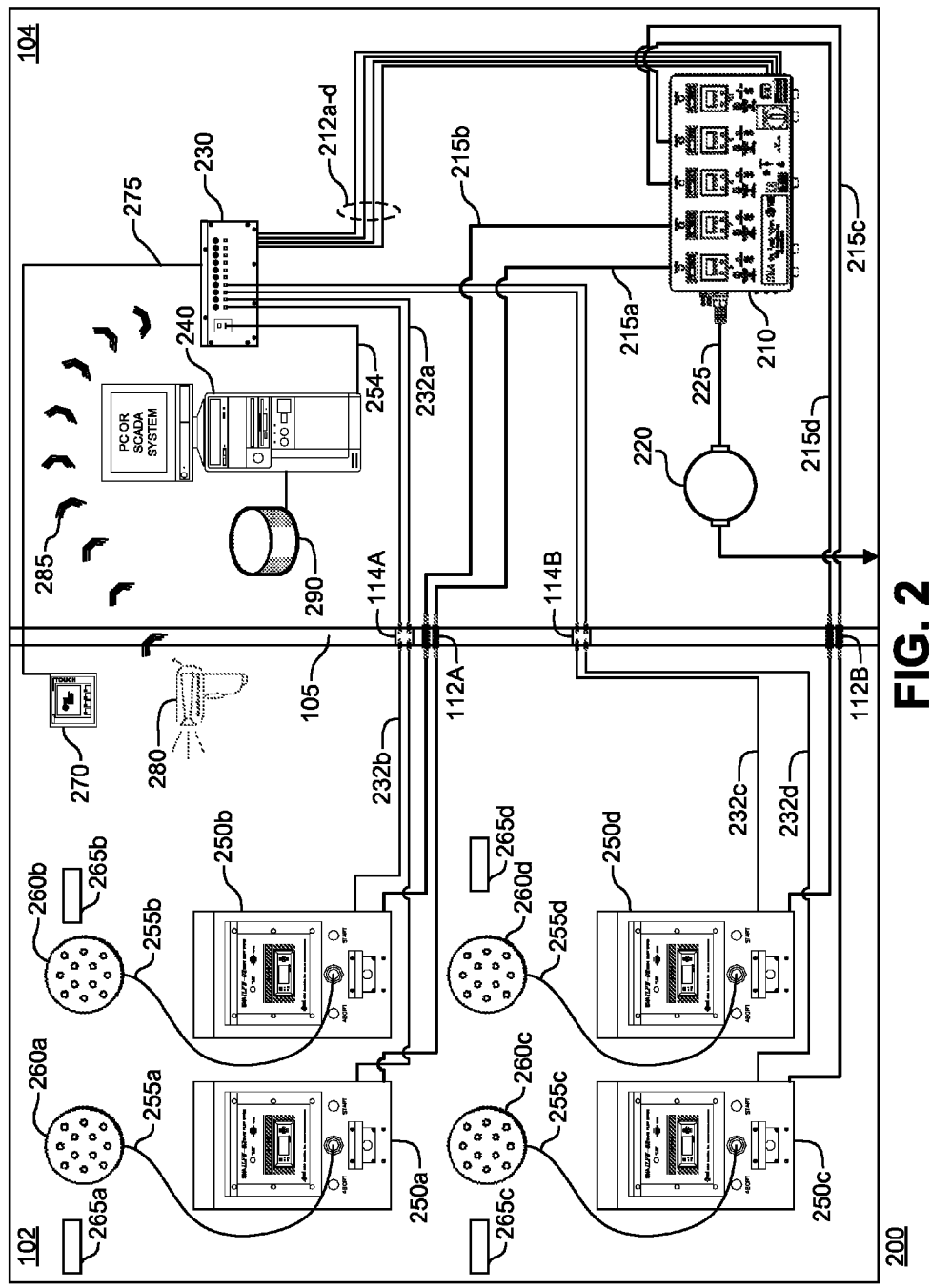
FIG. 2 is a schematic diagram of a tracking/logging and air sampling/monitoring system for use in the clean room of FIG. 1, in accordance with an exemplary embodiment of the present invention.

Turning now to FIG. 2, shown therein is a schematic diagram of a tracking/logging and air sampling/monitoring system 200, in accordance with an exemplary embodiment of the present invention. The system 200 is configured for use in tracking and logging data regarding a plurality of subjects and air sampling and incubation processes applied to the plurality of subjects. During air sampling, air from the clean room 102 is drawn over the subjects of the system 200 to collect contaminants present in the air of the clean room 102.

The system 200 includes a controller 210 (front view shown), a vacuum pump 220, an optional purge pump (not illustrated), an inline flow control base station 230, and a personal computer (PC) or System Control and Data Acquisition (SCADA) system 240, all of which may be co-located together in the adjacent space 104, adjacent to or remote from (i.e., not directly adjacent to) the clean room 102. An example of a controller suitable for use as the controller 210 is any of the SMA DDC Multi-Location Control Centers made by Veltek Associates, Inc., Malvern, Pa.

The system 200 further includes a plurality of inline flow control modules 250a, 250b, 250c, and 250d and a plurality of air sampling devices 260a, 260b, 260c, and 260d, all of which may be co-located together in the clean room 102. In the exemplary embodiment of the system 200 illustrated in FIG. 2 and described herein, the system 200 comprises four inline flow control modules 250a through 250d respectively connected to four air sampling devices 260a through 260d. It is to be understood that the number of inline flow control modules 250a through 250d and air sampling devices 260a through 260d is not limited by the system 200 to any particular quantity of inline flow control modules 250 or air sampling devices 260. That is, the system 200 is linearly scalable to substantially any number, n, of inline flow control modules 250a through 250n and any number, n, of air sampling devices 260a through 260n, wherein n is preferably 10. The air sampling devices 260a through 260d may be any known air sampling device for collecting a volume of air. Preferably, the system 200 comprises the same number of air sampling devices 260a through 260 as inline flow control modules 250a through 250n. It is contemplated, however, that the system 200 may include more air sampling devices 260 than inline flow control modules 250 so that one or more of the inline flow control modules 250 is coupled to more than one air sampling device 260. An example of an air sampling device suitable for use as the air sampling devices 260 is described in U.S. application Ser. No. 13/088,641 ("the '641 Application"), entitled "System and Method for Air Sampling in Controlled Environments," filed Apr. 18, 2011, and published as U.S. Pat. App. Pub. No. 2011/0205073, the contents of which are incorporated herein by reference.

The system 200 further includes subjects 265a, 265b, 265c, and 265d, which are disposed in respective air sampling devices 260a, 260b, 260c, and 260d, at various sites within the clean room 102. The air sampling devices 260a through 260d are positioned to collect airborne contaminants in the clean room 102 using the subjects 265a through 265d. Specifically, the air sampling devices 260a through 260d are used to collect the air surrounding respective subjects 265a through 265d, i.e., to draw air over the subjects 265a through 265d during air sampling, so that contaminants in the air of the clean room 102 at sites of interest are collected by the subjects 265a through 265d. After sampling air for a desired length of time, the subjects 265a through 265d are incubated if the expected airborne contaminants are bacteria, viruses, or fungi.

The terms "collecting," "sampling," "monitoring," and the like are not used to refer just to whole air sampling devices, but also to refer to devices that process the flow of fluid in order to separate certain gases, vapors, and particulate matter in the fluid for subsequent analysis and quantification. The terms "air" and "fluid" are used interchangeably to refer to gases, vapors, and particulates. Thus, "air sampler" does not mean that only air is being collected and/or monitored.

As shown, a separate inline flow control module 250a through 250d is associated with each air sampling device 260a through 260d. Each air sampling device 260a, 260b, 260c, and 260d is connected to its respective inline flow control module 250a, 250b, 250c, and 250d by a respective atrium air flow line 255a, 255b, 255c, and 255d, and each inline flow control module 250a, 250b, 250c, and 250d is connected to the controller 210 by a respective vacuum air line 215a, 215b, 215c, and 215d, each of which may be ¼-inch (0.6-cm) (inside diameter) vacuum tubing on the clean room 102 side of the system 200 and ⅜-inch (1.0-cm) (inside diameter) vacuum tubing on the adjacent space 104 side of the system 200. Other sized tubing may also be used.

The controller 210 includes four modular ports, such as the modular ports described and illustrated in the '641 Application. Each of such ports is connected a respective one of the vacuum air lines 215a through 215d. Via these ports, the controller 210 is configured to draw in air from the air sampling devices 260a through 260d and through the atrium air flow lines 255a through 255d and the vacuum air lines 215a through 215d to provide for the air sampling performed by the air sampling devices 260a through 260d.

The vacuum air lines 215a and 215b are connected across the wall 105 via a wall-mounted quick disconnect outlet 112A, and the vacuum air lines 215c and 215d are connected across the wall 105 via a wall-mounted quick disconnect outlet 112B. The outlets 112A and 112B are located on the wall 105 in between the clean room 102 and the adjacent space 104.

The controller 210 connects the inline flow control modules 250a through 250d to the vacuum pump 220 via a vacuum air line 225. Within the controller 210 is a manifold (not shown) that ties all of the individual vacuum air lines 215 together and connects them to the vacuum side of the vacuum pump 220 via the vacuum air line 225. The controller 210 includes individual solenoids (not shown) which are associated with the vacuum air lines 215 and are used to turn on the air flow to each inline flow control module 250a through 250d and their respective air sampling devices 260a through 260d so that any combination of the air sampling devices 260a through 260d can be employed simultaneously to perform sampling cycles at various locations throughout the clean room 102. In one exemplary embodiment, the controller 210 is configured so that each atrium air flow line 255a through 255d and vacuum air line 215a through 215d carries 1 CFM (28.3 liters/min) of air, which is the desired air flow rate needed to conduct a proper sampling cycle at the air sampling devices 260a through 260d. In another exemplary embodiment, the controller 210 is configured to allow for the air flow rates to be individually set, as described below.

The controller 210 communicates with the inline flow control modules 250a through 250d by way of the inline flow control base station 230 to receive data and commands from the inline flow control modules 250a through 250d and to provide data to the inline flow control modules 250a through 250d. The controller 210 includes four communication ports, each of which is connected to the inline flow control base station 230 via a respective electrical connection 212a, 212b, 212c, and 212d. The inline flow control base station 230 is connected to each of the inline flow control modules 250a through 250d via a respective electrical connection 232a, 232b, 232c, and 232d. The electrical connections 232a and 232b are connected across the wall 105 via a connector 114A, and the electrical connections 232c and 232d are connected across the wall 105 via a connector 114B. The controller 210 may contain any of the functionality of any of the controllers described in the '641 Application to control the vacuum pump 220 and communicate with the inline flow control modules 250a through 250d.

The various inline flow control modules 250a through 250d are shown connected in a parallel manner to the inline flow control base station 230 via the electrical connections 232a through 232d, and base station 230 is shown connected in a parallel manner to the controller 210 via the electrical connections 212a through 212d. It is to be understood, however, that the controller 210, the inline flow control base station 230, and the inline flow control modules 250a through 250d can be connected in any suitable manner. For example, in an exemplary alternative embodiment, the inline flow control modules 250a through 250d have network addresses, and the controller 210 communicates with the different inline flow control modules 250a through 250d by use of those network addresses via a common connection (e.g. a single electrical connection 212, such as may be used in an Ethernet network or wireless local area network (LAN)).

The exemplary embodiment of the system 200 illustrated in FIG. 2 illustrates four electrical connections 212a through 212d and four electrical connections 232a through 232d, each of which corresponds to a respective one of the inline flow control modules 250a through 250d and the air sampling devices 260a through 260d. It is to be understood that the number of electrical connections 212a through 212d and electrical connections 232a through 232d is not limited by the system 200 to any particular quantity of electrical connections. That is, the system 200 is linearly scalable to substantially any number, n, of electrical connections 212a though 212n and electrical connections 232a through 232n. Furthermore, although the controller 210, the inline flow control base station 230, and the inline flow control modules 250a through 250d are shown in wired communication with one another, it is to be appreciated that these components of the system 200 may communicate wirelessly, in an alternative exemplary embodiment of the system 200.

The base station 230 includes internal interfaces (not illustrated) for interfacing with the controller 210, and the controller 210 includes internal interfaces (not illustrated) for interfacing with the base station 230. The base station 230 forwards data (e.g., flow rates, alarm conditions, etc.) and commands (e.g., to start and/or stop air flow) received from the inline flow control modules 250a through 250 over respective electrical connections 232a through 232d to the controller 210 via the respective electrical connections 212a through 212d. The controller 210 receives such data and commands. The base station 230 also forwards data and commands received from the controller 210 via the electrical connections 212a through 212d to the inline flow control modules 250a through 250 over respective electrical connections 232a through 232d. Various examples of data and commands transmitted by the inline flow control modules 250a through 250 and the base station 210 are described below.

The PC or SCADA system 240 is also connected to the base station 230 via an electrical connection 254 and also includes an internal interface for communicating with the base station 230, and, likewise, the base station 230 includes an internal interface for interfacing with the PC or SCADA system 240. The base station 230 may forward all data and commands provided by the inline flow control modules 250a through 250 and the controller 210 to the PC or SCADA system 240 for tracking and monitoring the system 200 in real time and logging the data and commands in a database 290 maintained by the PC or SCADA system 240. Although the system 200 is described and illustrated herein as including the database 290, it is to be understood that the system 200 is not so limited. In other exemplary embodiments, the element 290 is a spreadsheet, a flat text file, or other data structure stored in a computer-readable medium.

The inline flow control modules 250a through 250d are configured to independently monitor various data during operation, e.g., during air sampling. Such data include any flow rates sensed by the respective inline flow control modules 250a through 250d, alarm signals generated by the respective inline flow control modules 250a through 250d, etc. For example, the inline flow control modules 250a through 250d monitor and display the actual flow rate that is realized at their respective air sampling devices 260a through 260d. If the flow rate in a respective vacuum air line 215a through 215d is off by +/−0.5% (i.e., not within the range of 0.95-1.05 CFM or 26.9-29.7 liters/min), then the corresponding inline flow control module 250a through 250d generates an alarm signal.

In an exemplary embodiment, each inline flow control module 250a through 250d includes an 8-second delay before the alarm signal is generated. That delay accounts for fluctuations that may occur during initial start-up of the system 200. A typical sampling cycle may last between 10 minutes and 3 hours.

An additional aspect of this exemplary embodiment provides that the base station 230 communicates any data and alarm signals received from the inline flow control modules 250a through 250d to the other inline flow control modules 250a through 250d, so that they may activate their respective visual alert indicators and audible alarms, and/or to the controller 210. The flow rates are communicated to the base station 210, where they are also monitored and controlled independently by the base station 210.

During operation, the controller 210 also monitors data relating to air sampling. For example, the controller 210 monitors flow rates through the ports of the controller 210, whether the individual ports of the controller 210 are powered up, and whether the ports are in an air sampling mode and/or are experiencing an air flow error during an air sampling cycle. The controller 210 may transmit any of such data to the base station 230 for sending to the inline flow control modules 250a through 250d. The detection of air flow rates performed by the inline flow control modules 250a through 250d is independent of the flow rate detection performed by the controller 210 so that the flow rates are simultaneously monitored at two locations for each air sampling device 260a through 260d during a sampling cycle, thereby adding an additional measure of safety through redundancy.

As depicted in FIG. 2, the system 200 further includes a touchpanel 270, which is connected to the inline flow control base station 230 via an electrical connection 275. The electrical connection 275 may be a wired or wireless communication. The touchpanel 270 may be co-located with the controller 210, or otherwise outside the clean room 102, or it may be co-located with the inline flow control modules 250a through 250d and the air sampling devices 260a through 260d in the clean room 102, as shown in FIG. 2. The touchpanel 270 includes an interface for communicating with the base station 230 for receiving data from the base station 230 and providing commands to the base station 230 for relaying to their proper destinations. It is to be understood that the touchpanel 270 may be configured to receive any data and commands provided to the base station 230 described herein.

For example, when the base station 230 and the touchpanel 270 communicate, the touchpanel 270 may receive data from the controller 210 collected during an air sampling period. As described above, such data may indicate whether the individual ports of the controller 210 are powered up, are in an air sampling mode, and/or experience an air flow error during an air sampling cycle. In that way, the touchpanel 270 can detect the state of activity of each of the individual ports of the controller 210, thereby allowing a user to determine where in the facility 100 air sampling is being conducted (i.e., which air sampling devices 260a through 260d are presently being operated, the time associated with a sampling cycle, etc.) and at which air sampling devices 260a through 260d any errors occur. Such data may further indicate the flow rates sensed in the inline flow control modules 250a through 250d, alarm conditions in the inline flow control modules 250a through 250d, etc. Thus, the touchpanel 270 may be used to display data, e.g., data collected during an air sampling period or other data described below, in real time regarding components of the system 200.

The touchpanel 270 may also be configured to provide commands to components of the system 200, such as the inline flow control modules 250a through 250d and the controller 210. For example, the touchpanel 270 also be used to remotely start and stop sampling at various air sampling devices 260a through 260d within the facility 100, thereby eliminating the need for the user to access the controller 210 or the inline flow control modules 250a through 250d directly to perform these functions. Thus, in an exemplary embodiment, the touchpanel 270 includes various input means, such as a touch screen, switches, or a mini-keyboard, that receive input from a user to signal to the controller 210 which air sampling devices 260a through 260d to operate. The touchpanel 270 communicates such commands to the controller 210 via the base station 230, thereby eliminating the need for the user to leave the location (room) of the touchpanel 270 to operate the controller 210 or the inline flow control modules 250a through 250d.

In an exemplary embodiment, the system 200 further includes a portable barcode scanner 280 for collecting data regarding the subjects 265a through 265d, a user operating the barcode scanner 280, and the rooms/sites in which the subjects 265a through 265d are located during air sampling and incubation periods of the subjects 265a through 265d. The barcode scanner 280 transmits such data wirelessly to the base station 230 by a wireless channel 285. The base station 230 may forward data received from the barcode scanner 280 to the touchpanel 270 for real-time display thereon. For example, the data may include identification data, location data, times and dates of scans, etc. for the subjects 265a through 265d, etc. The touchpanel 270 receives such data on the subjects 265a through 265d scanned by the barcode scanner 280 via the controller 210, in real time, and displays it. The touchpanel 270 may be configured to receive a user selection to view such data for only a selected one of the subjects 265a through 265d. In an exemplary embodiment, the barcode scanner 280 comprises a computer display which prompts the user 500 to scan the subjects 265a through 265d, the user 500's barcode 510, and the room/sites barcodes.

In another exemplary embodiment, the touchpanel 270 includes, or is connected to, a barcode scanner, which is configured to have functionality similar to that of the portable barcode scanner 280 for collecting data regarding the subjects 265a through 265d, the user of the touchpanel 270, and the rooms/sites in which the subjects 265a through 265d are located during air sampling and incubation. After scanning a barcode using the barcode scanner connected to the touchpanel 270, the touchpanel 270 transmits the scanned data to the base station 230 by the electrical connection 275.

In an exemplary embodiment, PC or SCADA system 240 monitors conditions in the clean room 102 and may monitor conditions in other rooms, e.g., other clean rooms 102 or rooms 104. The PC or SCADA system 240 includes software that includes a graphical representation of the different components of the system 200, e.g., images representing the front of the controller 210, the inline flow control modules 250a through 250d (or the inline flow control modules 250a and/or the wall panel disconnects 250a', described below), the touchpanel 270, and the portable barcode scanner 280. The PC or SCADA system 240 may include software to render such representations, receive real-time data from the base station 230 for these components, and display the real-time data in the representations to create a real-time "virtual" reproduction of the system 200. The PC or SCADA system 240 may also be configured to control the system 200, similarly to the touchpanel 270.

The PC or SCADA system 240 may also be configured to collect and store data regarding the operation of the components of the system 200 and commands provided by components of the system 200. Data recorded by the PC or SCADA system 240 may include data obtained during an air sampling period (the period of time over which the subjects 265a through 265d collect airborne contaminants from a clean room, such as the clean room 102) and data obtained during an incubation period (the period of time over which the contaminants in the subjects 265a through 265d, if they are viruses, bacteria, or fungi, are incubated). Such data may include data scanned by a barcode scanner, data inputted by a user, and data monitored by the inline flow control modules 250a through 250d and the controller 210. The PC or SCADA system 240 receives the data and commands for storage from the base station 230 and stores them in the database 290 or other memory.

Data obtained during an air sampling period may include any of the following inputted or scanned data: (1) identification data of the subjects 265a through 265d obtained by a barcode scanner; (2) location data of the subjects 265a through 265d obtained by or generated by the barcode scanner; (3) the date and time such location data was obtained, i.e., when the scan was performed; (4) identification data of the person operating the barcode scanner; and (5) the date and, optionally, time (obtained by the barcode scanner) the subjects 265a through 265d expire. Data obtained during the air sampling period may also include any of the following monitored data: (1) the flow rate at each individual air sampling device 260a through 260d; (2) the dates and times of the measured flow rates; (3) flow alerts/alarms generated at the inline flow control modules 250a through 250d; (4) indications of whether the individual ports of the controller 210 are powered up; (5) indications of whether the individual ports of the controller 210 are in an air sampling mode; (6) air flow errors detected by the controller 210; and (7) flow rates detected by the controller 210. It is to be understood that the date and time data for the scan may be automatically generated by an internal electronic clock within the barcode scanner 280, the base station 230, the touchpanel 270, or the PC or SCADA system 240. Alternatively, such date and time data may be manually entered by the user using the barcode scanner.

Data obtained during the incubation period include any of the following: (1) identification data of the subjects 265a through 265d obtained by a barcode scanner; (2) location data of the subjects 265a through 265d obtained by or generated by the barcode scanner; (3) the date and time such location data was obtained, i.e., when the scan was performed; (4) identification data of the person operating the barcode scanner; (5) and remarks entered by a user. It is to be understood that the date and time data for the scan may be automatically generated by an internal electronic clock within the barcode scanner, the base station 230, the touchpanel 270, or the PC or SCADA system 240. Alternatively, such date and time data may be manually entered by the user using the barcode scanner.

The base station 230 is the gateway of data and commands received from the various components of the system 200 and forwarded to the PC or SCADA system 240, which may log the data and commands in the database 290 for later retrieval and/or which may provide for real-time monitoring and display by the PC or SCADA system 240. In an additional exemplary embodiment, the touchpanel 270 may access the historical data, such as past identification data, location data, dates, times, etc., logged by the PC or SCADA system 240 in the database 290. Using the touchpanel 270, an operator may request information about a selected subject 265a through 265d. The touchpanel 270 receives such selection and forwards it to the controller 210. The controller 210 forwards the selection to the PC or SCADA system 240, which responds with the desired historical data. For example, using the touchpanel 270, the operator selects one of the subjects 265a through 265d. The controller 210 responds with identification data, historical location data, historical times and dates of scans, etc. for the selected subject 265a through 265d. The touchpanel 270 displays such historical data.

To facilitate the real-time monitoring of the system 200 and the logging of data regarding the system 200, the PC or SCADA system 240 includes any suitable computing processor or processing platform that is capable of performing the functions and operations of the exemplary embodiments of the PC or SCADA system 240 described herein, e.g., real-time monitoring of data and commands in the system 200, tracking and logging of data and commands of the system 200 in the database 290, and recalling of historical data stored in the database 290. The PC or SCADA system 240 includes a computer-readable medium comprising software code stored thereon that, when executed by the PC or SCADA system 240, causes the PC or SCADA system 240 to perform any of the functionality of the PC or SCADA system 240 described herein. Thus, all or parts of the functionality of the PC or SCADA system 240 that provide for remotely monitoring the system 200, storing data and commands in the database 290, and retrieving stored (historical) data from the database 290 may be stored as computer-readable software instructions in a computer-readable media and retrieved from the computer-readable media and executed to perform the functions of the PC or SCADA system 240 described herein.

The computing platform for the PC or SCADA system 240 is desirably a personal computer or server, either in a stand-alone system or as part of a network. It is also contemplated that the PC or SCADA system 240 may be a laptop computer, a tablet PC, a Personal Digital Assistant (PDA), a smart phone, etc. The PC or SCADA system 240 desirably includes a display for a user to monitor the status of the various components of the system 200 and includes a user input, such as a keyboard, key pad, or touch screen, for the user to input instructions for controlling the system 200, selectively monitoring components of the system 200, or recalling historical data from the database 290. It is to be understood that the PC or SCADA system 240 can be connected to any number of systems 200 at any number of locations, thereby providing a mechanism for monitoring and controlling multiple clean rooms 102 from a single, central location. And, the same functionality may be provided via a secure website from which a user can remotely monitor and control any number of systems 200 over the Internet from virtually any location, adding yet another degree flexibility and accessibility to the present invention.

Referring now to FIGS. 3A and 3B, there are respectively illustrated a front view and a side cross-sectional view of the inline flow control module 250a, in accordance with an exemplary embodiment of the present invention. It is to be understood that any or all of the inline flow control modules 250b through 250d in the system 200 may be configured as the inline flow control module 250a illustrated in FIGS. 3A and 3B and described below.

The inline flow control module 250a includes a housing 310 having a digital air flow switch interface 320, a stop switch 330, a start switch 340, dual alert/alarm indicators 350 (visual) and 360 (audible), an air flow plug adapter 355, and an air flow switch 380. The inline flow control module 250a is electrically connected to the base station 230 via the electrical connection 232a and is fluidly connected to the controller 210 via the vacuum air line 215a and to the air sampling device 260a via the atrium air flow line 255a, which is removably connectable to the air flow pug adapter 355.

The digital air flow switch interface 320 is configured for receiving set points for the flow rates in the vacuum air line 215a and the atrium air flow line 255a from a user. The digital air flow switch interface 320 includes a digital LED display 325 and various buttons 322 that allow the user to set the desired range of flow rates in the vacuum air line 215a and the atrium air flow line 255a. The digital air flow switch interface 320 communicates these set points to the controller 210 to control the air flow through the vacuum air line 215a and the atrium air flow line 255a during an air sampling cycle.

The start switch 340 is used to manually activate an air sampling period. In response to the start switch 340 being activated, the inline flow control module 250a sends a signal to the controller 210 via the base station 230, which may also forward the signal to the PC or SCADA system 240 for logging in the database 290. The controller 210 activates the vacuum pump 220 to cause an air flow in the vacuum air line 215a, the air flow plug adapter 355, and the atrium air flow line 255a at the flow rate set in the digital air flow switch interface 320.

The stop switch 330 aborts the sampling cycle and turns off the vacuum air flow for the air sampling device 260a. When the stop switch 330 is activated, a stop signal is sent to the controller 210 via the inline flow control base station 230, which may also forward the signal to the PC or SCADA system 240 for logging. In response, the controller 210 closes off the vacuum air line 215a from the vacuum pump 220. The user may abort the sampling cycle for various reasons, including that an alert/alarm has been signaled by the inline flow control module 250a.

The digital air flow switch 380 is configured for monitoring the air flow rate in the vacuum air line 215a and the atrium air flow line 255a and for detecting airflow errors (e.g., 1 CFM errors) during a sampling cycle. Specifically, the air flow switch 380 measures the air flow rate through the vacuum air line 215a and compares it to the set flow rate. The digital air flow switch 380 generates a flow alert/alarm when the flow measured for the air sampling device 260a is outside specification (e.g., not within the range of 0.95-1.05 CFM or 26.9-29.7 liters/min). The alert/alarm indicators 350 and 360 then indicate. Both a visual alert indicator 350, such as an LED, and an audible alarm 360, such as a buzzer, are provided to alert the user when the flow rate is out of specification. The alert and alarm continue until the stop switch 330 is activated, or the error conditions are removed, and the flow rate returns to the desired level (e.g., 1 CFM or 28.3 liters/min).

In accordance with an exemplary embodiment of the inline flow control module 250a, air flow is only activated and de-activated in the vacuum air line 215a when the user manually operates the start switch 340 and the stop switch 330, respectively. That way, the user can verify that the air sampling device 260a connected to the inline flow control module 250a is properly set up and ready to perform a sampling cycle. However, it should be appreciated that the system can be configured so that the user can start and stop air flow to other or all of the inline flow control modules 250b through 250d configured as the inline flow control module 250a in the system 200, either simultaneously or at other times, at any of the inline flow control modules 250a through 250d, or at either the controller 210, the inline flow control base station 230, the PC or SCADA system 240, or the touchpanel 270.

The air flow plug adapter 355 is provided on the front face of the housing 310 of the inline flow control module 250a and is adapted to connect to the atrium air flow line 255a to connect to the air sampling device 260a. The plug adapter 355 is preferably a quick disconnect so that the atrium air flow line 255a can be quickly connected and disconnected and replaced, if necessary. The inline flow control module 250a can be mounted either internally to the wall 105 or externally on the face of the wall 105. The electronics of the inline flow control module 250a may be sealed inside the housing 310 so that the device may be disinfected like other portions of the clean room 102.

FIG. 3B shows the internals of the inline flow control module 250a, including the air flow switch 380, which couples the vacuum air line 215a to the plug adapter 355, so that the atrium air flow line 255a may be easily connected and disconnected from the vacuum air line 215a. In an exemplary embodiment, the air flow switch 380 is a digital air flow switch that may be constructed similarly to the air flow switches within the controller 210.

The air flow switch 380 is configured to detect the flow rate coming in from the atrium air flow line 255a connected to the plug adapter 355 and passing through to the vacuum air line 215a. The air flow switch 380 generates an alarm signal if the detected air flow rate is not within the parameters set by the user, e.g., 1 CFM or 28.3 liters/min. If an alarm signal is generated, the alert/alarm indicators 350 and 360 are activated and an alarm signal is forwarded to the base station 230.

The electrical connection 232a is connected to a data port on the air flow switch 380 and to the alert/alarm indicators 350 and 360. Data regarding the flow rate detected by the air flow switch 380 and alarm conditions generated by the air flow switch 380 are transmitted, optionally with a date and time stamp, to the controller 210 via the base station 230. In addition, the flow rate coming in from the atrium air flow line 255a and passing through to the vacuum air line 215a is also sensed and monitored by the controller 210 independently from the flow rate detection performed by the air flow switch 380 in the inline flow control module 250a so that the flow rate is simultaneously monitored at two locations during a sampling cycle. All such data and optional date and time stamps may be transmitted to the PC or SCADA system 240 via the base station 230 for storage.

For example, the air flow switch 380 may identify an error in the flow rate from the air sampling device 260a due to a break in the vacuum air line 215a between the controller 210 and the inline flow control module 250a, which is particularly advantageous when the vacuum air line 215a is within the wall 105 or near noisy equipment such that a break would otherwise be difficult to detect. The air flow switch 380 may also identify an error in the flow rate from the air sampling device 260a where either the atrium air flow line 255a or the vacuum air line 215a is kinked or not properly connected. And, the air flow switch 380 may identify if the vacuum pump 220 is not turned on or working properly. When identified, such problems can be corrected without affecting any other sampling devices 260b through 260d.

As also illustrated in FIGS. 3A and 3B, the inline flow control module 250a further includes a barcode scanner 370, which is electrically connected to the electrical connection 232a to communicate with the base station 230 and the controller 210. As described in further detail below, the barcode scanner 370 is configured to collect data regarding the subject 265a, such as identification data for the subject 265a and the date and time the subject 265a was scanned by the barcode scanner 370, for transmission back to the base station 230. It is to be understood that the barcode scanner 370 may include functionality that is similar to the barcode scanner connected to the touchpanel 270 and the barcode scanner 280.

Referring now to FIGS. 4A and 4B, there are respectively illustrated a front view and a side cross-sectional view of a wall panel disconnect, generally designated as 250a', in accordance with an exemplary embodiment of the present invention. In an exemplary embodiment of the system 200, the wall panel disconnect 250a' may replace any of the inline flow control modules 250a through 250d as wall panel disconnects 250a' through 250d'.

The wall panel disconnect 250a' includes a panel 410, to which the plug adapter 355 and the barcode scanner 370 are mounted. The plug adapter 355 is connected to the vacuum line 215a, which communicates back to the controller 210. The barcode scanner 370 is connected to the electrical connection 232a, which communicates back to the base station 230. Also mounted to the panel 410 of the wall panel disconnect 400 is the air sampling device 260a, which is coupled to the plug adapter 355 and the vacuum line 215a by the atrium air flow line 255a.

The wall panel disconnect 250a' is simplified from the inline flow control module 250a. The wall panel disconnect 250a' does not include start and stop switches, flow monitoring, or alarming, as the flow control module 250a does. Rather, such functionality resides in the controller 210, the PC or SCADA system 240, or the touchpanel 270. For example, airflow through the atrium air flow line 255a, the plug adapter 355, and the vacuum line 215a is monitored by a respective flow control switch in the controller 210. The wall panel disconnect 250a' does not include a digital air flow switch, such as the air flow switch 380 included in the inline flow control module 250a. As described in further detail below, the barcode scanner 370 is configured to collect identification information, such as information identifying the air sampling device 260a, for transmission back to controller 210 via the base station 230.

As described above, the inline flow control modules 250a through 250d and the wall panel disconnects 250a' through 250d' each include a barcode scanner 370. The system 200 also includes an optional barcode scanner connected to the touchpanel 270 and/or an optional barcode scanner 280. Any of these barcode scanners may be used to collect data relating to the subjects 265a through 265d during operation of the system 200.

Figure 5:
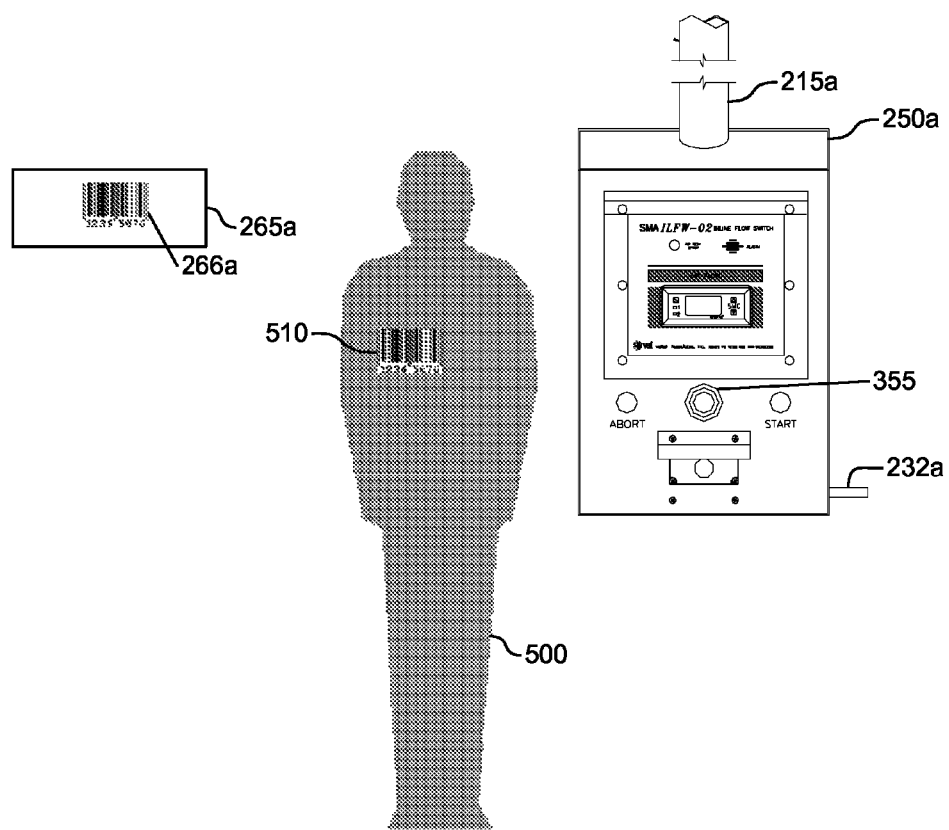
FIG. 5 illustrates an exemplary subject for collecting airborne contaminants, the subject including a barcode encoded with information regarding the subject, in accordance with an exemplary embodiment of the present invention.

FIG. 5 illustrates an exemplary embodiment of the subject 265a, which is subjected (exposed) to the environment of the clean room 102 to collect contaminants in the air of the clean room 102 during an air sampling period and then placed into incubation after a period of exposure in the clean room 102 if the contaminants are bacteria, viruses, and/or fungi, in accordance with an exemplary embodiment of the present invention. The subject 265a includes a barcode 266a, which includes encoded information about the subject 265a. Such information may include any of the following: (1) an expiration date of the subject 265a; (2) a lot number of the subject 265a; (3) media and fill of the subject 265a (in embodiments in which the subject 265a is an agar plate); and (4) an identification code (identification data) uniquely identifying the subject 265a compared to other subjects which may be sampled by the system 200. In an exemplary embodiment, the identification code for the subject 265a comprises a date the barcode 266a was generated and a unique serial number appended thereto. In an alternative exemplary embodiment, this date is replaced with the lot number.

The user 500 may be associated with a barcode 510, which is worn on an ID badge or contained on an ID card. The barcode 510 includes encoded information about the user 500. Such information may include an identification code (identification data) uniquely identifying the user 500 compare to all other users. Finally, the room and site within the room in which the subject 265a is located may include a barcode (not illustrated), which includes encoded information about the room and site, such as a unique ID code for the room and a unique ID code for the site within the room. Although FIG. 5 illustrates the subject 265a including the barcode 266a and description below is made with reference to the subject 265a and the barcode 266a, it is to be understood that description herein relating to the subject 265a and the barcode 266a applies to the subjects 265b through 265d and their barcodes 266b through 266d. Further, although FIG. 5 illustrates the barcodes 266a and 510 as one-dimensional barcodes, other embodiments in which they are two-dimensional barcodes are contemplated.

During the air sampling period, the user 500 uses a barcode scanner, such as the barcode scanner connected to the touchpanel 270, the barcode scanner 280, or the barcode scanner 370, to scan the barcode 266a of the subject 265a to retrieve the information encoded within the barcode 266a. The user 500 may also use the barcode scanner to scan the barcode 510 to retrieve the information about the user 500 encoded within the barcode 510 and the barcode(s) identifying the location of the subject 265a (room and site at which the subject 265a is situated). During the incubation period, the user 500 uses the barcode scanner to scan the barcode 266a to retrieve the information encoded within the barcode 266a. The user 500 may also use the barcode scanner to scan the barcode 510 to retrieve the information about the user 500 encoded within the barcode 510 and the barcode(s) identifying the location of the subject 265a (room and site at which the subject 265a is situated).

The barcode scanner receives the information encoded within the barcodes as optically encoded signals. The barcode scanner converts the optically encoded signals to electrical signals encoded with the information contained within the barcodes. The barcode scanner decodes the information and transmits it to the base station 230. The base station 230 forwards the information to the PC or SCADA system 240 for storage and/or real-time tracking, and optionally to the touchpanel 270 for real-time presentation. In an exemplary embodiment, the information encoded within the barcode 266a is stored by the PC or SCADA system 240 in association with the user information from the barcode 510. By logging when and where the subject 265a is located, the system 200 is able to electronically track the subject 265a as it is exposed to contaminants in an environment.

In an exemplary embodiment, the date and times of the scans may be inputted by the user 500 into the barcode scanner and sent to the PC or SCADA system 240 to provide a time stamp to the scan stored in the PC or SCADA system 240. Alternatively, in another exemplary embodiment, the PC or SCADA system 240 or the barcode scanner may automatically generate the time stamp. Furthermore, in exemplary embodiments in which the barcode scanner used is stationary, such as the barcode scanner 370 or the barcode scanner connected to the touchpanel 270, such barcode scanner may be configured to provide the location data for the room and site of the scan, thereby obviating the need to scan a barcode for location data for the room and site.

Referring now to FIG. 6, there are illustrated exemplary steps of a method 600 of performing air sampling, in accordance with an exemplary embodiment of the present invention. The method 600 is described with reference to using the barcode scanner connected to the touchpanel 270, the barcode scanner 280, or the barcode scanner 370 of the inline flow control module 250a when conducting air sampling using the inline flow control module 250a. It is to be understood that operation of any of the inline flow control modules 250b through 250d or the wall panel disconnects 250a' through 250d' during air sampling may be similar to the operation of the inline flow control module 250a described below.

At the start of the air sampling period, the user 500 uses the barcode scanner to scan the barcode 266a to retrieve the information encoded within the barcode 266a, Step 602. Optionally, in the Step 602, the user 500 also uses the barcode scanner to scan the barcode 510 to retrieve the information about the user 500 encoded within the barcode 510 and/or to scan barcode(s) located at the air sampling room/site containing location information about the sampling room/site and/or to enter remarks regarding the scan. In a Step 604, all scanned information, any entered remarks, and location information regarding the scan site are decoded and transmitted to the base station 230. The base station 230 forwards this information to the PC or SCADA system 240 for storage and/or real-time tracking and/or to the touchpanel 270 for real-time presentation. The PC or SCADA system 240 stores this information in a new record in the database 290.

After scanning the barcode 266a and the optional user barcode 510 and room/site barcode(s), the subject 265a is placed into the inline flow control module 250a by the user 500, Step 606. The user 500 depresses the start button 340 to start the air sampling cycle. The air sampling device 260a samples air surrounding the subject 265a, which air flows to the controller 210 via the vacuum air line 215a at a flow rate set in the inline flow control module 250a in the Step 606.

At the conclusion of the air sampling cycle in the Step 606, the user 500 re-scans the barcode 266a and may, optionally, scan the barcode 510 and/or the barcode(s) (if present) located at the air sampling room/site containing location information about the air sampling room/site and/or may enter remarks regarding the scan, Step 608. In a Step 610, all scanned information, any entered remarks, and location information regarding the air sampling site obtained in the scan in the Step 608 are decoded and transmitted to the base station 230. The base station 230 forwards this information to the PC or SCADA system 240 for storage and/or real-time tracking and/or to the touchpanel 270 for real-time presentation. The method 600 concludes with the user 500 or another person transporting the subject 265a to incubation, Step 612.

Referring now to FIG. 7, there are illustrated exemplary steps of a method 700 of incubating the subject 265a, in accordance with an exemplary embodiment of the present invention. The method 700 is described with reference to using the barcode scanner connected to the touchpanel 270, the barcode scanner 280, or the barcode scanner 370 of the inline flow control module 250a when incubating the subject 265a.

At the start of the incubation period, the user 500 uses the barcode scanner to scan the barcode 266a to retrieve the information encoded within the barcode 266a, Step 702. Optionally, in the Step 702, the user 500 also uses the barcode scanner to scan the barcode 510 to retrieve the information about the user 500 encoded within the barcode 510 and/or to scan barcode(s) located at the air sampling room/site containing location information about the sampling room/site and/or to enter remarks regarding the scan. In a Step 704, all scanned information, any entered remarks, and location information regarding the scan site are decoded and transmitted to the base station 230. The base station 230 forwards this information to the PC or SCADA system 240 for storage and/or real-time tracking and/or to the touchpanel 270 for real-time presentation. The PC or SCADA system 240 stores this information in a new record in the database 290.

After scanning the barcode 266a and the optional user barcode 510 and room/site barcode(s), the subject 265a is placed into incubation by the user 500, Step 706. During the air incubation period, the user 500 may periodically re-scan the barcode 266a, log observations/remarks regarding the subject 265a, and may, optionally, scan the barcode 510 and/or the barcode(s) (if present) located at the incubation room/site containing location information about the incubation room/site, Step 708. In a Step 710, all scanned information, any entered remarks, and location information regarding the room/site obtained in the Step 708 are decoded and transmitted to the base station 230. The base station 230 forwards this information to the PC or SCADA system 240 for storage and/or real-time tracking and/or to the touchpanel 270 for real-time presentation.

At the conclusion of incubation, the user 500 again scans and/or enters information in the Step 708. In the Step 710, all scanned information, any entered remarks/observations, and location information regarding the incubation room/site obtained in the final scan in the Step 708 are decoded and transmitted to the base station 230. The base station 230 forwards this information to the PC or SCADA system 240 for storage and/or real-time tracking and/or to the touchpanel 270 for real-time presentation. The method 700 concludes with the PC or SCADA system 240 transferring the records in the database 290 for the subject 265a electronically to the cognizant department, Step 712.

In an exemplary embodiment, the PC or SCADA system 240 is configured to analyze the records in the database 290 for a room/site to determine any trends in air contaminants. The PC or SCADA system 240 determines if a number of colonies in the subject 265a meets or exceeds a predetermined number (an alert level). If so, the PC or SCADA system 240 issues an alert, logs the alert in the database 290, and notifies the cognizant department of a possible contamination problem in the room/site. The PC or SCADA system 240 also determines if the number of subjects from a room/site in alert meets or exceeds, or if the number of colonies in the subject 265a meets or exceeds, a predetermined number (an alarm level), the predetermined number for the alarm level being greater than the predetermined number for the alert level. If so, the PC or SCADA system 240 issues an alarm, logs the alarm in the database 290, and notifies the cognizant department of a possible contamination problem in the room/site. The alert and alarm levels for each room/site may be set by a quality control department.

In an exemplary embodiment, in the Steps 604 and 610 during air sampling and in the Steps 704 and 710 during incubation, the barcode scanner 370 of inline flow control module 250a or the barcode scanner connected to the touchpanel 280 also transmits an identification code of the barcode scanner to the base station 230. The identification code of the barcode scanner identifies the location of the barcode scanner and, hence, the location of the scan, e.g., where air sampling or incubation may be taking place. In such embodiment, the user 500 need not scan the barcode located at the air sampling or incubation site to obtain the location information as it is automatically transmitted by the barcode scanner in the Steps 604, 610, 704, and 710.

Illustrated in FIG. 8 is a method 800 by which data relating to a subject is scanned and transferred to the PC or SCADA system 240, in accordance with an exemplary embodiment of the present invention. The method 800 comprises two Steps 802 and 804. The Step 802 is a scanning step corresponding to the Steps 602, 608, 702, and 708 of the methods 600 and 700 in which barcodes are scanned using the barcode scanner connected to the touchpanel 270, the barcode scanner 280, or the barcode scanner 370 and decoded and in which data is entered into the barcode scanner by the user 500. The Step 804 is a data transmission step corresponding to the Steps 604, 610, 704, and 710 of the methods 600 and 700, in which data is transmitted to the base station 230 and then to the PC or SCADA system 240 for storage in the database 290. The PC or SCADA system 240 stores the received data in the database 290 and may also analyze the data and transmit a response indicating whether the correct subject was sampled and/or that the subject is not expired. The response may be displayed on the touchpanel 270, the barcode scanner 280, or the digital air flow switch interface 320. The method 800 illustrates the scanning and transmission steps of the methods 600 and 700 in greater detail.

The method 800 is now described with reference to FIGS. 2 and 5. In the Step 802, a scan in the room/site is initiated, Step 802*a*. After beginning the scan, the user 500, using the barcode scanner, scans the barcode 266*a* on the subject 265*a*, Step 802*b*. The barcode scanner decodes the information in the barcode 266*a* and temporarily stores it. The user 500 may also enter any remarks regarding the scan. The barcode scanner temporarily stores the inputted remarks.

In an exemplary embodiment of the Step 802, after the Step 802*b* is performed, the method 800 skips Step 802*c*. In such exemplary embodiment, the barcode scanner itself is programmed with location information. Thus, barcode(s) for the room/site need not be scanned, and Step 802*c* may be skipped. Additionally, in this exemplary embodiment, the barcode scanner or the PC or SCADA system 240 provides the time and date information, although it is contemplated that the user 500 may enter the time and date into the barcode scanner. The method 800 may proceed to a Step 802*d* for scanning the barcode for the user 500. It is contemplated, however, that this step may also be skipped in variations on this exemplary embodiment. If it is performed, the barcode scanner decodes the information in the barcode 510 and temporarily stores it.

In another exemplary embodiment of the Step 802, after the Step 802*b* is performed, the method proceeds to the Step 802*c*. The user 500 scans separate barcode(s) for the room/site, e.g., clean room ID. The barcode scanner decodes the information in the room/site barcode(s) and temporarily stores it. Additionally, in this exemplary embodiment, the barcode scanner or the PC or SCADA system 240 provides the time and date information, although it is contemplated that the user 500 may enter the time and date into the barcode scanner. The method 800 may proceed to a Step 802*d* for scanning the barcode 510 for the user 500. It is contemplated, however, that this step may also be skipped in variations on this exemplary embodiment. If it is performed, the barcode scanner decodes the information in the barcode 510 and temporarily stores it.

After all data is inputted and/or scanned in the Step 802, the method 800 proceeds to the Step 804. In this step, the barcode scanner transmits all scanned information, inputted information, and any inputted remarks as a batch to the base station 230, Step 804*a*. The base station 230 forwards the information and remarks to the PC or SCADA system 240. The PC or SCADA system 240 creates a new record in the database 290 for the received data and stores the received data in the new record.

The PC or SCADA system 240 analyzes the data received during the method 800 and provides a response, via an electronic message, to the room/site, Step 804*b*. The response may indicate whether the subject 265*a* is the correct subject for the room/site and is not expired. The method 800 is complete.

Illustrated in FIG. 9 is an exemplary table 900 stored in the database 290, in accordance with an exemplary embodiment of the present invention. The table 900 comprises a category 910 for date/time data, a category 920 for location data, a category 930 for identification data, and an optional category 940 for remarks. In the exemplary embodiment illustrated in FIG. 9, the date/time category comprises a date field 910*a* and a time field 910*b*; the category 920 comprises a room ID field 920*a* and a site ID field 920*b*; the category 930 comprises a field 930*a* for the ID of the subjects 265*a* through 265*d* and a field 930*b* for the ID of the users (e.g., the user 500); and the category 940 comprises a field 940*a* for remarks.

The table 900 illustrates exemplary data stored by the PC or SCADA system 240 in the database 290 during air sampling and incubation periods. In the exemplary embodiment of the table 900 illustrated in FIG. 9, each record of the table 800 includes data obtained during execution of the method 800 in either of the Step 602 of the method 600 or the Step 702 of the method 700. Record 1 was generated during performance of the Step 602 in the method 600 of air sampling. The field 910*a* of Record 1 indicates that an agar plate (subject) was scanned on Feb. 16, 2011. The field 910*b* indicates that the time of the scan was 10:22 p.m. The fields 920*a* and 920*b* indicate that the agar plate was located in a room 119 and at a site designated as "Bench." The field 930*a* indicates that the agar plate had an ID of "SMA 001," and the field 930*b* indicates that the person who scanned the agar plate SMA 001 was Tom. Record 2 indicates that the agar plate having an ID of SMA 001 was scanned at the bench in Room 119 a short time (i.e., after completion of a sample cycle) after the time indicated in Record 1 by a different tech ID.

Records 3-5 were generated during performance of the Step 702 in the method 700 of incubation. For Records 3-5, the field 930*a* indicates that the agar plate was SMA 001; the field 920*a* indicates that the room has changed to room 104; and the site within room 104 is "Incubation." The field 940*a* of Record 4 indicates that 2 colonies have been observed in agar plate SMA 001 during incubation, in which case the colonies have reached an alert level and an alert message is to be sent to a cognizant quality control department. The field 940*a* of Record 5 indicates that 3 colonies have been observed during incubation, in which case the colonies have reached an alarm level and an alarm message is to be sent to a cognizant quality control department. Thus, Record 5 indicates that the air around the Bench site in room 119 included airborne contaminants around the times of 10:22 p.m. through 11:25 p.m. on Feb. 16, 2011 in an amount sufficient to trigger an alarm.

The table 900 includes data for three other agar plates: SMA 005, SMA 010, and SMA 011. The Records 6-10 pertain to the agar plate SMA 005, which was located in room 119 at site "LFM" during an air collection period (see Field 920a of Records 6-7) and in room 104 during an incubation period (see Field 920a of Records 8-10). The field 940a for Record 9 indicates that 2 colonies have been observed during incubation, an amount which is deemed safe for the LFM site. The field 940a for Record 10 indicates that 5 colonies have been observed during incubation, in which case the colonies have reached an alert level and an alert message is to be sent to a cognizant quality control department. Thus, Record 10 indicates that the air around the LFM site in room 119 included airborne contaminants around the times of 10:26 p.m. through 11:30 p.m. on Feb. 16, 2011 in an amount sufficient to trigger an alert.

The Records 11-15 pertain to the agar plate SMA 010, which was located in room 2120 at site "Fill 1" during an air sampling period (see Field 920a of Records 11-12) and in room 104 during an incubation period (see Field 920a of Records 13-15). The field 940a for Record 14 indicates that no colonies have been observed during incubation. The field 940a for Record 15 indicates that 1 colony has been observed during incubation, in which case the colonies have reached an alert level and an alert message is to be sent to a cognizant quality control department. Thus, Record 15 indicates that the air around the Fill 1 site in room 2120 included airborne contaminants around the times of 1:00 p.m. through 2:15 p.m. on Feb. 16, 2011 in an amount sufficient to trigger an alert.

Finally, the Records 16-20 pertain to the agar plate SMA 011, which was located in room 2120 at site "Fill 2" during an air sampling period (see Field 920a of Records 16-17) and in room 104 during an incubation period (see Field 920a of Records 18-20). The field 940a for Records 19 and 20 indicates that one colony has been observed during incubation. Thus, Record 20 indicates that the air around the Fill 2 site in room 2120 included airborne contaminants around the times of 1:10 p.m. through 1:15 p.m. on Feb. 16, 2011 in an amount not sufficient to trigger and alert or alarm.

Figure 10:
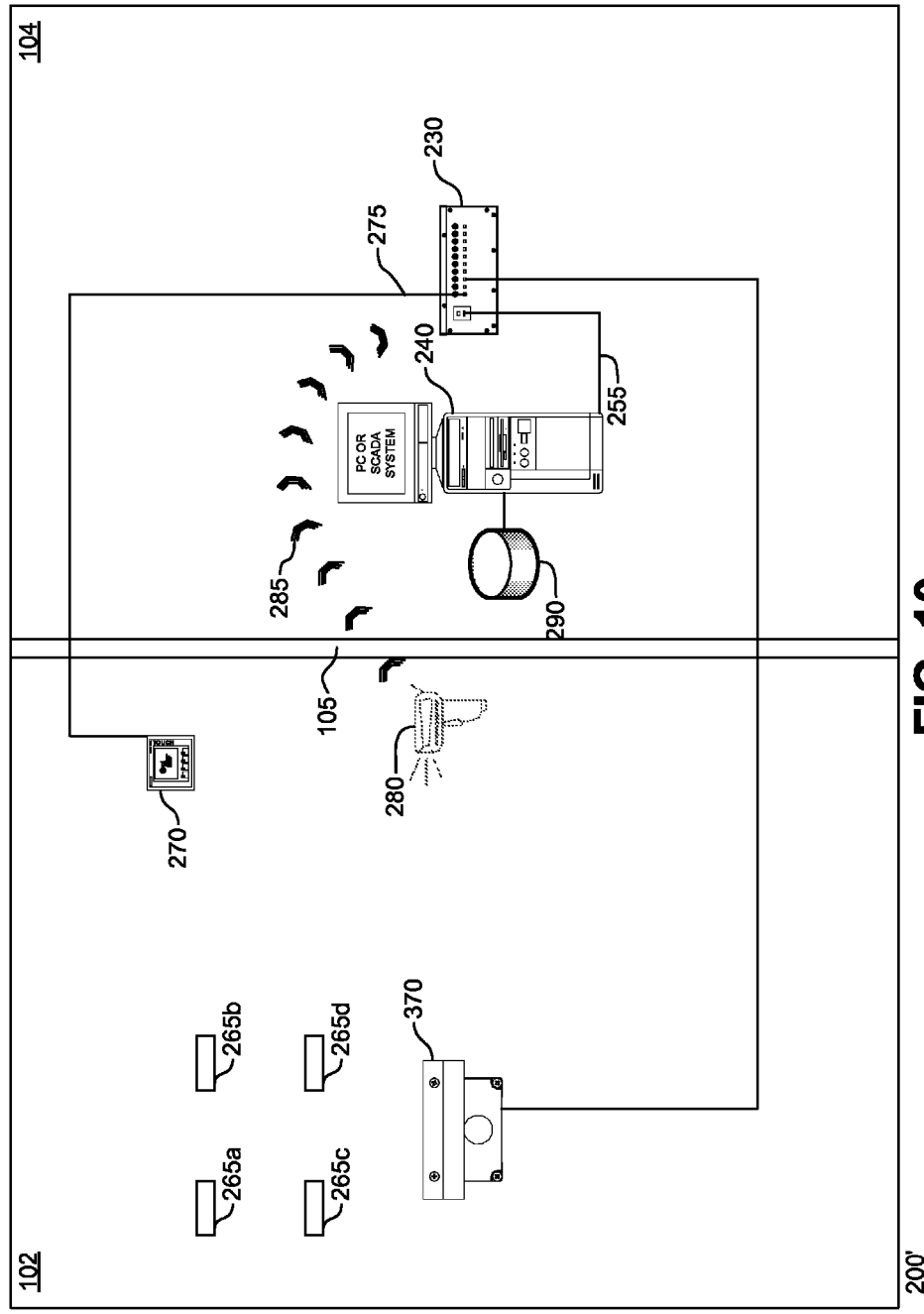
FIG. 10 illustrates an exemplary alternative embodiment of the tracking/logging and air sampling/monitoring system of FIG. 1, in accordance with an exemplary embodiment of the present invention.

It is to be understood that the system 200 and the methods 600 through 800 are not limited to use with subjects 265a through 265d which are incubated. Thus, although the subjects 265a through 265d may include liquid impingers, such as agar plates, they may also instead use air filters, glass-plate impactors, cascade impactors, or inertial samplers for collecting airborne contaminants. Further, it is to be understood that the tracking and monitoring of the subjects 265a through 265d described herein may be used in an exemplary alternative embodiment of the system 200, generally designated in FIG. 10 as 200', that does not include a controller 210, a vacuum pump 220, and a plurality of inline flow control modules 250a, 250b, 250c, and 250d. Instead, in the system 200', the subjects 265a through 265d collect contaminants via other methods. The subjects 265a through 265d are tracked, monitored, and logged during collection and incubation according to the method 600 through 800 using the barcode scanners, the controller 230, the PC or SCADA system 240, and the database 290 in the system 200' without the air-sampling components of the system 200.

Although the system 200 is described as including a barcode scanner and the subjects 265a through 265d are described as including respective barcodes 266a through 266d as are the user 500 (barcode 510) and the rooms and sites, it is to be understood that the system 200 is not limited to use with barcodes. Other identification tags and identification readers are contemplated. In an alternative embodiment, the system 200 includes an RFID reader, rather than barcode readers, and all of the barcodes are replaced by RFID tags. Further, in embodiments in which the identification tags are barcodes, it is to be understood that the barcodes may be linear barcodes (as shown) or 2D (matrix) barcodes.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

What is claimed is:

1. A system for tracking subjects that collect airborne particles, each of the subjects including a subject identification tag encoded with identification information identifying the each subject, the system comprising:
   a plurality of air sampling devices, each configured to draw air over one of the subjects during air sampling;
   an identification reader configured to scan one of the subject identification tags and decode the identification information encoded within the scanned subject identification tag;
   a computer configured to receive and store the decoded identification information; and
   a controller connected to each of the air sampling devices via vacuum lines that separately controls air flow rates at each of the air sampling devices.

2. The system of claim 1, further comprising:
   a plurality of inline flow control modules, each inline flow control module corresponding to one of the plurality of air sampling devices, each of the inline flow control modules configured to separately measure the air flow realized at the corresponding air sampling device,
   wherein the controller is connected to each of the air sampling devices via one of the inline flow control modules.

3. The system of claim 1, wherein:
   the subjects are respectively disposed in one or more locations, each location comprising a location identification tag encoded with location information; and
   the identification reader is further configured to:
     scan the location identification tag in the location of the subject that includes the scanned subject identification tag; and
     decode the location information encoded within the scanned location identification tag.

4. The system of claim 3, wherein the computer is further configured to receive and store the decoded location information.

5. The system of claim 4, wherein the computer is further configured to compare the decoded location information to the decoded identification information to determine whether the subject that includes the scanned subject identification tag is properly located.

6. The system of claim 5, wherein the computer is further configured to transmit an indication of whether the subject that includes the scanned identification tag is properly located.

7. The system of claim 5, further comprising:
a database for storing scanned information received from the identification reader,
wherein the computer is further configured store the decoded identification information and the decoded location information in a record in the database.

8. The system of claim 7, wherein the computer stores a time stamp in the record in the database.

9. The system of claim 1, wherein the computer is further configured to receive and store data obtained during the period when each air sampling devices draws air over each subject.

10. The system of claim 9, wherein the data includes the air flow rate at each of the air sampling devices.

11. A method for tracking subjects that collect airborne particles, each of the subjects including a subject identification tag encoded with identification information identifying the each subject, the method comprising:
providing a plurality of air sampling devices, each configured to draw air over one of the subjects during air sampling;
providing a controller connected to each of the air sampling devices via vacuum lines;
scanning, by an identification reader, one of the subject identification tags;
decoding the identification information encoded within the scanned subject identification tag;
storing the decoded identification information;
separately controlling, by the controller, air flow rates at each of the air sampling devices; and
drawing air over the subject that includes the scanned subject identification tag.

12. The method of claim 11, further comprising:
providing a plurality of inline flow control modules, each inline flow control module corresponding to one of the plurality of air sampling devices, wherein the controller is connected to each of the air sampling devices via one of the inline flow control modules; and
separately measuring, by the inline air flow control modules, the air flow rates at each of the air sampling devices.

13. The method of claim 11, wherein the one or more subjects are respectively disposed in one or more locations, each location comprising a location identification tag encoded with location information, the method further comprising:
scanning, by the identification reader, the location identification tag in the location of the subject that includes the scanned subject identification tag; and
decoding the location information encoded within the scanned location identification tag.

14. The method of claim 3, further comprising:
storing the decoded location information.

15. The method of claim 4, further comprising:
comparing the decoded location information to the decoded identification information to determine whether the subject that includes the scanned subject identification tag is properly located.

16. The method of claim 5, further comprising:
transmitting an indication of whether the subject that includes the scanned subject identification tag is properly located.

17. The method of claim 5, further comprising:
storing the decoded identification information and the decoded location information in a record in a database.

18. The method of claim 7, further comprising:
storing a time stamp in the record in the database.

19. The method of claim 1, further comprising
receiving and storing, by the computer, data obtained during the period when each air sampling devices draws air over each subject.

20. The method of claim 9, wherein the data includes the air flow rate at each of the air sampling devices.

* * * * *